United States Patent [19]
Feldman et al.

[11] Patent Number: 5,095,431
[45] Date of Patent: Mar. 10, 1992

[54] METHOD AND SYSTEM FOR CALIBRATING AN X-RAY SCANNER BY EMPLOYING A SINGLE NON-CIRCULAR STANDARD

[75] Inventors: Andrei Feldman, Paris; Dominique Cornuejols, Palaiseau, both of France

[73] Assignee: General Electric CGR S.A., Issy les Moulineaux, France

[21] Appl. No.: 324,545

[22] Filed: Mar. 16, 1989

[30] Foreign Application Priority Data

Mar. 25, 1988 [FR] France .................. 88 03583

[51] Int. Cl.$^5$ ............ G06F 15/42; A61B 6/00; G01D 18/00
[52] U.S. Cl. ............... 364/413.13; 378/207
[58] Field of Search ............ 378/18, 207; 250/252.1 R; 364/413.13

[56] References Cited

U.S. PATENT DOCUMENTS

| | | | |
|---|---|---|---|
| 4,225,789 | 9/1980 | Albrecht | 378/207 X |
| 4,331,869 | 5/1982 | Rollo | 378/207 X |
| 4,352,020 | 9/1982 | Horiba et al. | 378/18 |
| 4,400,827 | 8/1983 | Spears | 378/207 |
| 4,497,061 | 1/1985 | Hounsfield | 378/18 |
| 4,663,772 | 5/1987 | Mattson et al. | 378/18 |
| 4,873,707 | 10/1989 | Robertson | 378/18 |

FOREIGN PATENT DOCUMENTS

| | | |
|---|---|---|
| 107253 | 5/1984 | European Pat. Off. . |
| 154429 | 9/1985 | European Pat. Off. . |
| 216507 | 4/1987 | European Pat. Off. . |
| 218367 | 4/1987 | European Pat. Off. . |
| 239647 | 10/1987 | European Pat. Off. . |
| 3412303 | 10/1985 | Fed. Rep. of Germany ...... 378/207 |

OTHER PUBLICATIONS

Gonzalez et al., *Digital Image Processing*, Addison-Wesley Pub. Co., 1987, pp. 163-175.

*Primary Examiner*—Jerry Smith
*Assistant Examiner*—David Huntley
*Attorney, Agent, or Firm*—Oblon, Spivak, McClelland, Maier & Neustradt

[57] ABSTRACT

The invention relates to x-ray scanners and more particularly to a method for calibrating scanners by means of a single standard of elliptical shape, for example. Attenuation measurements are performed with respect to a number of principal angular positions of the scanner about the standard. In addition, a number of meaurements or views are taken on each side of this principal position in order to compute a mean attenuation with respect to each channel. The attenuation curve is then smoothed by filtering and polynomial approximation.

7 Claims, 3 Drawing Sheets

METHOD AND SYSTEM FOR CALIBRATING AN X-RAY SCANNER BY EMPLOYING A SINGLE NON-CIRCULAR STANDARD

BACKGROUND OF THE INVENTION

1. Field of the Invention

The invention relates to x-ray scanners and more particularly to a method for calibrating devices of this type which makes use of a single non-circular standard and to a system for the application of said method.

2. Description of the Prior Art

In order to examine a patient, it is becoming an increasingly common practice to make use of x-ray devices known as scanners which produce images of cross-sections of the patient. These devices are based on the physical phenomenon of absorption of x-rays by the human body. This absorption is directly related to the distance x traveled by x-rays within the body in accordance with the formula:

$$I = I_0 e^{-bx}$$

where:
- $I_0$ is the intensity of radiation entering the human body
- $I$ is the intensity of radiation emerging from the human body,
- $b$ is a coefficient of attenuation which depends on the body being traversed.

In a logarithmic measurement scale, the attenuation $I/I_0$ is equal to $bx$ or in other words is proportional to the distance x.

As shown in FIG. 1, these devices are essentially constituted by an x-ray source 10 associated with a detection device 11, these two elements being disposed in a fixed geometrical relationship with respect to each other in such a manner as to ensure that the body to be examined can be interposed between them. In addition, they are supported by a structure (not shown in the drawings) which is capable of rotating about the body to be examined so as to irradiate the body at different angles. The x-ray source which is controlled by a device 13 emits its rays in an angular sector which is of sufficient width to illuminate the entire cross-section of the body. The detection device 11 has the shape of an annular sector, the length of which is adapted to the width of the x-ray beam and is constituted by a large number of elementary detectors 12 in juxtaposed relation.

In order to obtain an image of the cross-section of the human body traversed by the x-ray beam, the structure which supports the source 10 and the detection device 11 is displaced in rotation about the body and the output signals of the elementary detectors 12 are measured for suitable processing in accordance with known methods in order to obtain an image which is representative of the cross-section. For this treatment, the elementary detectors 12 (also known as channels) are connected to an electronic device 14 which first computes the logarithm of the signals received so as to obtain a signal whose amplitude is proportional to the attenuation of the x-rays.

As a result of different phenomena which will not be explained here, the amplitude of the aforementioned signal in the case of each elementary detector or channel is not proportional to the attenuation which has in fact been sustained. In consequence, in order to remedy this drawback, consideration has been given to various methods which consist for example in recording the output signals of the channels in the presence of bodies having known dimensions and a known coefficient of absorption in order to compute the attenuations (logarithm calculations) and to compare these measured attenuations with values computed as a function of the dimensions and of the absorption coefficient of the body or standard. These comparisons make it possible to deduce a law of correspondence or a modifying law between the measured values and the values which should be obtained. This law can be in the form of correspondence files or of mathematical formulae representing this correspondence in respect of each detection channel.

By way of example, the standards which are employed for performing these so-called calibration measurements are shims having different thicknesses which are introduced in proximity to the x-ray source, thus entailing the need for handling operations at the level of the source in order to insert and remove said shims. Furthermore, the shape of these shims and their position are far removed from the shape and position of the body of the patient to be examined, thus increasing the non-linearity of the system.

In U.S. Pat. No. 4,352,020, it is proposed to employ circular shims 15 to 17 having different diameters which are disposed at the center of rotation of the support structure. This makes it possible to come closer to the conditions of measurements which will be made on the body to be examined. This patent also proposes to make use of a standard in the form of a circular-section cone which is displaced transversely with respect to the beam so as to obtain different lengths of attenuation. With the standards described, the measurements are performed in respect of a predetermined position of the support structure and in the case of each standard.

FIG. 2 shows the shape of three response curves 20, 21 and 22 of attenuation as a function of the position of the channels in the case of measurements on three standards of circular shape. The measured values are represented by the dots and vary in the vicinity of a mean value which represents the theoretical value in a linear system. These curves can be employed as follows: when the measured signal corresponds to a point A, it will be deduced therefrom that the linear signal is the point A' of the mean curve 20. When the measured signal corresponds to a point B located between the curves 20 and 21, the linear signal will be deduced therefrom by interpolation between the curves 20 and 21. This interpolation can be computed in accordance with a linear law or more generally a polynomial law.

The curves 23 and 24 of FIG. 3 show in a different form the principle of calibration at the level of a channel. These curves describe within a given channel the attenuation as a function of the thickness x in the case of measured values (curve 23) and in the case of computed values (straight line 24). In fact, the measured values give points which are joined to each other in accordance with a predetermined law, namely either linear or polynomial, so as to obtain a continuous curve. When measuring an attenuation, this corresponds for example to point C of curve 23 and there is deduced therefrom the linear value corresponding to point C' of curve 24.

The U.S. patent cited earlier describes a device in which the correspondence between the measured values and the real values of attenuation is effected by a system of files created during the calibration operation.

In regard to interpolation, the patent proposes linear, cubic and biquadratic interpolations but only the linear interpolation is described in detail.

The methods of calibration which have been briefly described in the foregoing suffer from a major disadvantage in that they call for the use of a number of standards, thus involving a large number of handling operations. Moreover, these handling operations have to be accurate, especially in the case of circular standards, the different centers of which must coincide with the center of rotation of the structure.

It is worthy of note that the U.S. patent proposes to employ a single standard which would have the shape given by FIG. 12 of said patent and to rotate the structure about said standard, thereby obtaining absorption paths of different lengths according to the angular position of the structure. However, this mode of operation is only mentioned and does not indicate either the method or the means for applying the method in this case.

SUMMARY OF THE INVENTION

One object of the present invention is to carry out a method of calibration which makes use of a single standard having a shape other than circular and in particular an elliptical shape or a shape which would be symmetrical with respect to two coplanar axes.

Another object of the present invention is to provide a system for carrying out said method.

The invention relates to a method for calibrating an x-ray scanner comprising an x-radiation source and an N-channel detection device by making use of a single standard having a shape other than circular, said method being distinguished by the fact that it involves the following operations:

a) positioning of the standard between the x-radiation source and the detection device;

b) measurement of attenuations in the N channels of the detection device in respect of P principal angular positions of the rotating structure and in respect of n elementary positions in close proximity to each other about each principal angular position;

c) computation of the mean value of the n attenuations in respect of each channel and in respect of each of the P principal angular positions;

d) smoothing of the N mean values of attenuations from one channel to the next in respect of each of P principal angular positions so as to obtain a curve of response of attenuation as a function of the position of the channel in which the high-frequency components have been eliminated, said response curve thus obtained being the real curve of variation of the attenuation introduced by the standard as a function of the respective position of the N channels.

The invention also relates to a system for carrying out the method of calibration, said system being distinguished by the fact that it comprises:

first means for computing the logarithm of the N signals delivered by the N channels, second means for computing in the case of each channel the attenuation introduced by the standard, third means for computing in the case of each channel the mean value of the n measured attenuations in respect of a given principal angular position, fourth means for computing the Fourier transform of the N mean attenuations corresponding to a principal angular position, fifth means for eliminating the high-frequency components in the spectrum resulting from the Fourier transform, sixth means for computing the inverse Fourier transform of the low-frequency components of the spectrum, seventh means for computing a polynomial approximation of the curve resulting from the inverse Fourier transform, and means for retaining in memory the values representing the polynomial approximation of each response curve relative to a principal angular position.

DETAILED DESCRIPTION OF THE INVENTION

Figure 1:
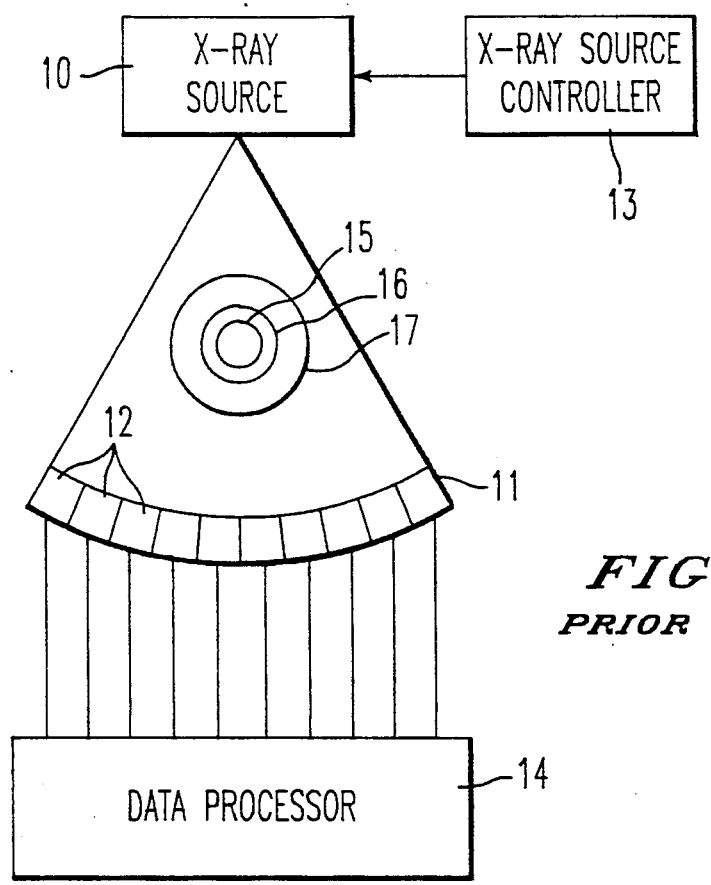
FIG. 1 is a schematic diagram of an x-ray scanner in which calibration is obtained by means of circular standards.
Figure 2:
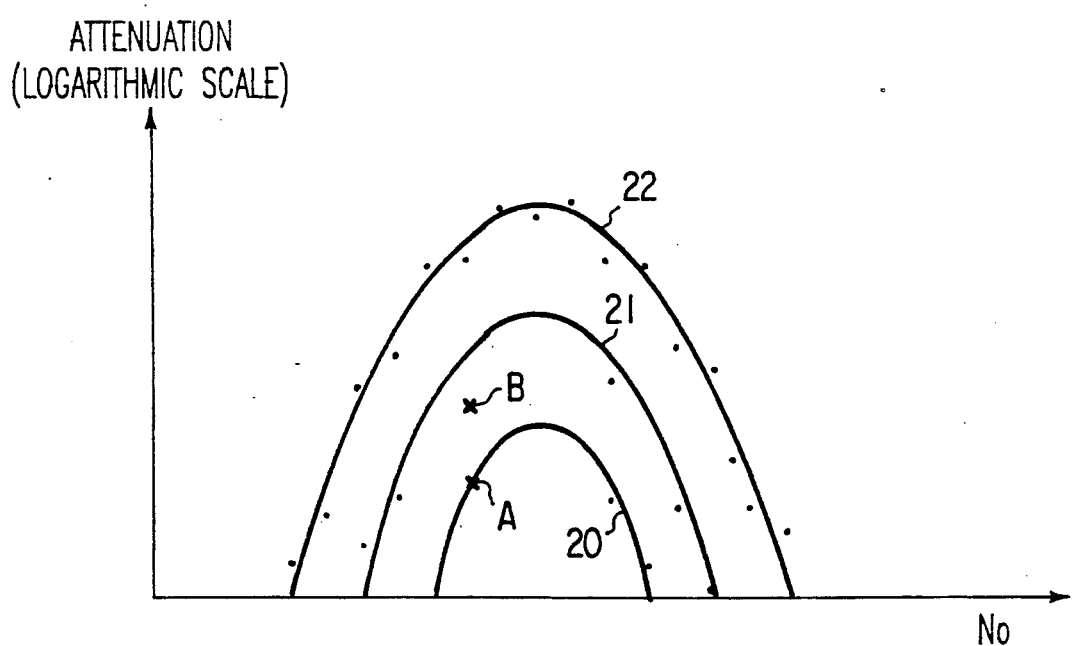
FIG. 2 is a diagram showing different curves of attenuation as a function of the position of the detectors or channels and of the diameter of the standard.
Figure 3:
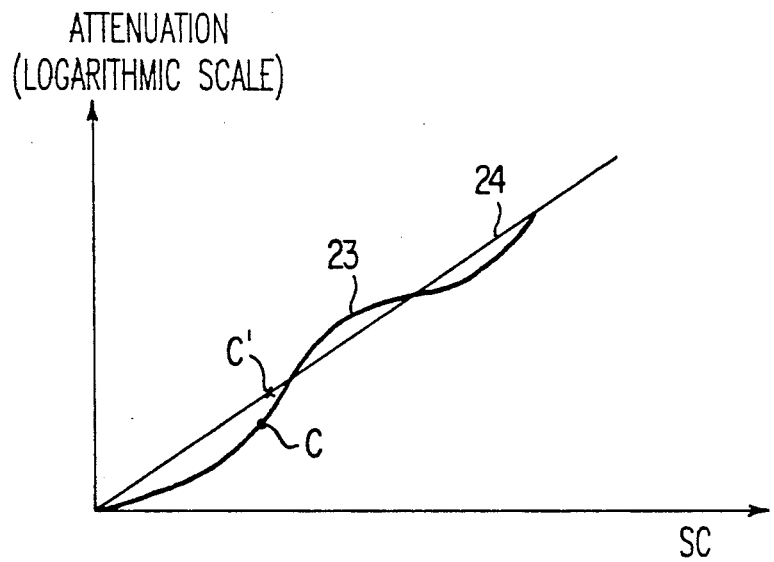
FIG. 3 is a diagram showing the curves of theoretical and measured attenuation in respect of a predetermined channel, as a function of the absorption path.

FIGS. 1, 2 and 3 have already served to define the prior art in the introductory part of this specification and will not be described further.

Figure 4:
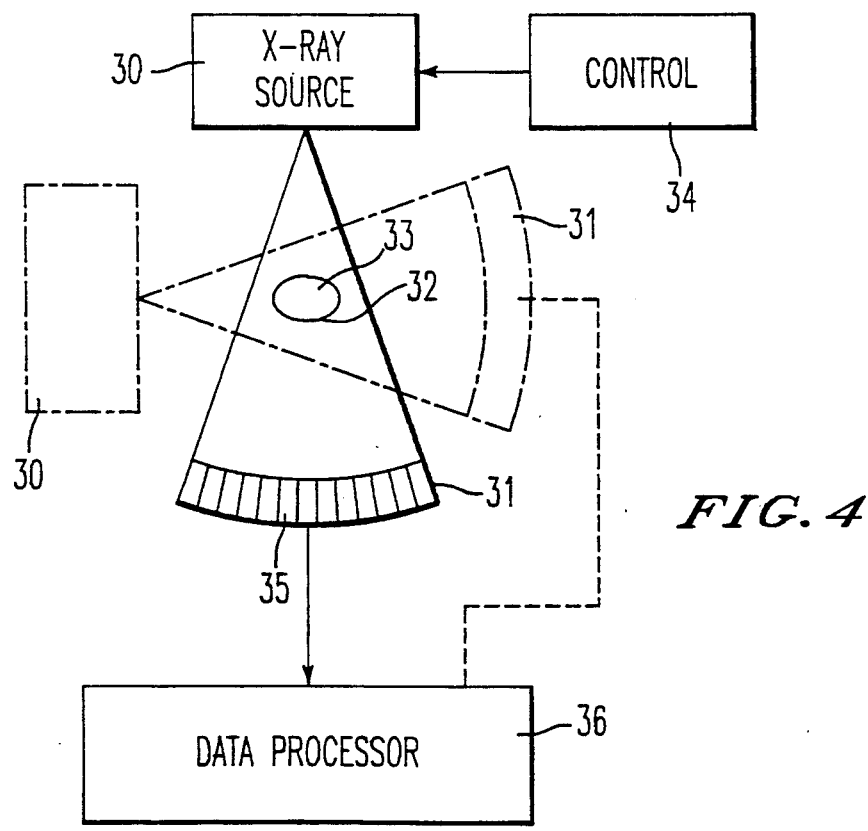
FIG. 4 is a schematic diagram of an x-ray scanner in which calibration is obtained in accordance with the characteristics of the invention.

The diagram of FIG. 4 is similar to that of FIG. 1 in that it shows a x-ray scanner comprising an x-ray source 30 and a detection device 31 having a plurality of detectors or channels 35 between which is interposed a patient's body in normal operation or a standard 32 of elliptical shape at the time of calibration operations. Although not shown in the drawings, a structure is provided for supporting the source 30 and the device 31 and for rotating the assembly about the patient's body or the standard, the axis of rotation being defined by the point 33 located within the standard but not necessarily at its geometrical center. The x-ray source 30 is controlled by a control device 34 whilst the different detectors or channels 35 of the device 31 are connected to an electronic system 36 which will be described with reference to FIG. 6.

The method of calibration in accordance with the invention consists in placing the support structure in different angular positions or so-called principal angular positions about the standard and in carrying out a series of attenuation measurements in each angular position and on each side of this position. By way of example, it is possible to choose sixteen principal angular positions uniformly spaced at 22°30′ and to perform, for example, ten elementary measurements on all the detection channels about each principal angular position. By way of example, if the number of detectors is 1024, the total number of views will be 16×10:160 and the total number of measurements will be 1024×160:163840. By way of example, each view about a principal angular position is separated by an angle of approximately one-third of a degree.

Accordingly, for each principal angular position, there are ten views on each of the 1024 channels or in other words ten measurements per channel in an angular sector of approximately three degrees and each measurement corresponds to a slightly different path within the standard and therefore to a slightly different attenuation. In accordance with the invention, in each channel, these ten measurements are employed for computing a mean value which makes it possible to improve the signal-to-noise ratio by a coefficient $\sqrt{10}$. These mean values which are sixteen in number serve to trace in respect of each principal angular position a curve of variation of attenuation as a function of the position of the channels. In fact, this number of curves can be reduced to four since the sixteen principal angular positions are reduced to four if the symmetries between the principal angular positions and those of the standard are taken into account.

Figure 5:
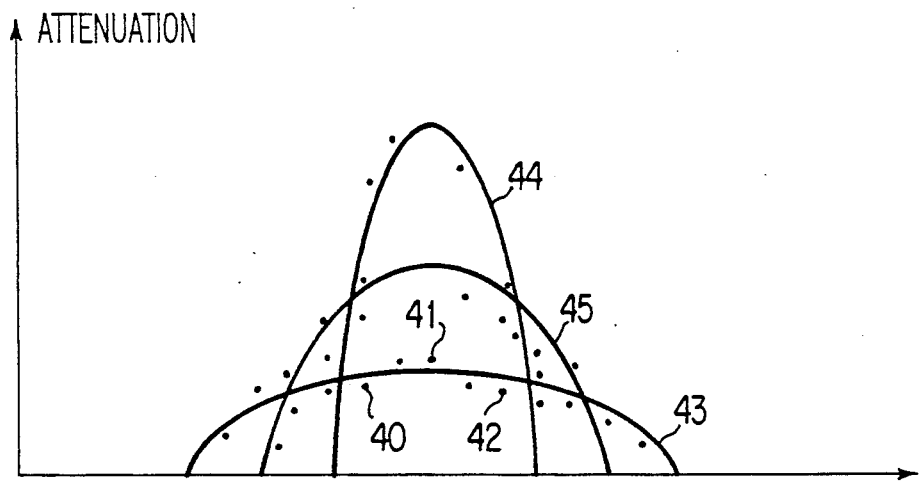
FIG. 5 is a diagram showing different curves of attenuation as a function of the position of the detector or channel and of the position of the x-ray source and of the detectors with respect to the single standard.

These curves of variation are shown in FIG. 5 in the case of three of the four principal angular positions after the symmetries have been taken into account. In this figure, the dots 40, 41 or 42 represent the mean values of attenuation for a certain number of the 1024 channels and curve 43 results from a smoothing operation in accordance with the present invention, this operation being described hereinafter with reference to FIG. 6.

Curve 43 corresponds to the angular position of FIG. 4 in which the elliptical standard 32 is irradiated along the major axis of the ellipse. Curve 44 corresponds to the angular position shown in dashed lines in FIG. 4 in which the standard 32 is irradiated along the minor axis of the ellipse. Finally, curve 45 corresponds to an intermediate position between the two positions mentioned above.

Moreover, as indicated in the foregoing, the sixteen principal angular positions are symmetrical in pairs, the two symmetrical positions being separated in pairs by an angle of 180°. These two symmetrical positions produce identical attenuation curves and only one need accordingly be retained. In fact, in accordance with the invention, it is proposed to combine the measurements obtained from these two symmetrical positions by determining their mean value in the manner which will be explained in greater detail with reference to FIG. 6. The signal-to-noise ratio is accordingly improved by a factor $\sqrt{2}$, namely a total of $\sqrt{20}$.

Furthermore, if use is made of a standard of symmetrical shape with respect to two axes such as orthogonal axes, for example, it is possible to group the measurements corresponding to positions which are symmetrical with respect to these axes. In consequence, the sixteen principal positions which have been reduced to eight by the first symmetry may again be grouped in pairs by determining their mean value, thus finally obtaining four principal angular positions. The signal-to-noise ratio is again improved by $\sqrt{2}$, namely a total of $\sqrt{40}$.

The principal aspects of the method of calibration in accordance with the invention are:
utilization of a non-circular standard;
measurement of output signals of the N channels in respect of P principal angular positions of the source-detector structure and in respect of n elementary positions or views which are close together about each principal angular position;
computation of the mean value of the n measurements in respect of each channel and in respect of each of the P principal angular positions;
smoothing of the mean values from one channel to the next in respect of each principal angular position so as to obtain a curve of response in which the high frequency components have been eliminated.

In the case of uniformly spaced and even-numbered principal angular positions, it is intended to compute the mean value of the measurements corresponding to principal positions spaced at 180°. Furthermore, if the standard has a symmetrical shape with respect to two axes, computation of the mean value is also carried out on the measurements obtained in respect of positions which are symmetrical with respect to said axes.

Figure 6:
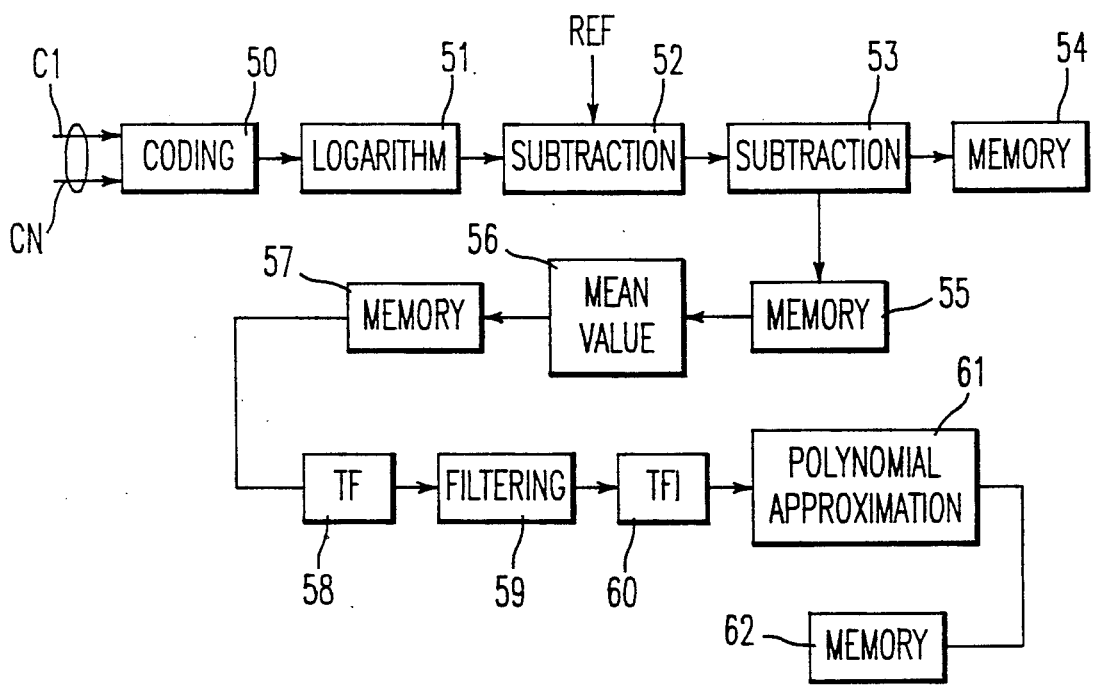
FIG. 6 is a functional diagram of a system for processing the output signals of the detectors.

In order to implement the method, it is proposed to construct a system in accordance with the functional diagram given in FIG. 6. In this figure, the signals delivered by the 1024 detectors are applied to a coding circuit 50 which supplies digital values or codes. These codes will be used for all the operations which will be described hereinafter and which can be carried out by means of a suitably programmed computer.

The N codes resulting from a measurement at an elementary position or view are applied to a logarithm computation circuit 51. The logarithmic values are subtracted in a circuit 52 from a reference logarithmic value REF delivered by a detector designated as a monitor which directly receives the x-radiation without attenuation. This difference therefore gives the value of attenuation introduced by the standard with respect to a path in the air. These N differential values, which each correspond to one channel, are then subtracted in a circuit 53 from N logarithmic attenuation values measured without any standard or in other words along paths in the air. These values have been measured and computed prior to said method of calibration and are subsequently employed in known manner at the time of measurements made on the patient. For this reason, they are recorded in a memory 54. This second subtraction operation makes it possible to take into account part of the disparities between the channels and therefore to suppress their influence from one channel to the next. The N values resulting from this second subtraction are recorded in a memory 55 which is designed to receive the N.P.n. codes which will result from the n measurements made (or n views taken) at n elementary positions about a principal angular position. The n.N. codes are used for computing the mean value on each channel by means of a circuit 56. The codes of the N mean values are recorded in a memory 57. It is understood that the memory 55 and the computing circuit 56 can be constructed in the form of an adding circuit which would carry out nine successive addition operations.

In order to benefit by the effects of symmetry of the P principal angular positions and of the standard, several modes of operation are open to choice. One mode consists in carrying out the measurements successively for four symmetrical principal angular positions and in determining the mean value for one channel, not on ten values but on forty values. This calls for a memory 55 designed to receive 40.N codes. Another mode of operation consists in making use of P memories 57, namely one memory per principal angular position, and in performing a second computation of the mean value on the values contained in the four memories corresponding to the four symmetrical principal angular positions.

After these operations involving computation of the mean value which have the principal object of reducing noise and therefore improving the signal-to-noise ratio, there then take place the smoothing operations which are of two orders. First of all, an operation involving elimination of the high-frequencies in the circuits 58, 59 and 60 and an operation involving polynomial approximation in a circuit 61.

The operation which involves elimination of the high frequencies first consists of a Fourier transform in the circuit 58 in order to obtain the spectrum of the signal on the N channels, then in low-pass filtering in the circuit 59 which removes the high-frequency components and, finally, an inverse Fourier transform so as to revert to the initial signal but without any high-frequency component.

The polynomial approximation operation in the circuit 61 can be limited to the central portion of the curves 43, 44 and 45 of FIG. 5. This operation is carried out by all known methods and means. The results of this polynomial approximation are recorded in a memory 62 which can contain the numerical values of the smoothed curves P, P/2 or P/4 depending on whether the above-mentioned symmetries are taken into account or not, the curves being computed one after the other.

The values recorded in the memory 62 at the end of the operations in respect of P principal angular positions constitute calibration values which are employed in known manner at the time of operations involving measurement on the patient so as to compute the real value of attenuation from the measured value.

Each smoothed curve of the memory 62 corresponds to a non-smoothed curve of the memory 57 and the difference between the values of these two curves in respect of one and the same channel makes it possible to compute a difference value. Thus when, in the case of this channel, the difference between the value measured with the patient and the smoothed value is within this difference value, it is accordingly deduced that the real value is that of the smoothed curve. When this difference exceeds said difference value, it is necessary to perform an interpolation computation of the linear or polynomial type in order to determine the real value between two smoothed curves.

The system for carrying out the method has been described in the form of functional circuits but it is clearly apparent that this system can be realized in the case of a computer in which the different operations hereinabove described are performed by programming.

What is claimed is:

1. A method for calibrating an x-ray scanner having an x-radiation source and an N-channel detection device with a single standard having a shape other than circular, comprising the steps of:
   a) positioning the standard between the x-radiation source and the detection device;
   b) measuring attenuations in the N channels of the detection device with respect to P principal angular positions of a rotating structure and with respect to n elementary positions or views in close proximity to each other about each principal angular position;
   c) computing the means value of the n attenuations with respect to each channel and with respect to each of the P principal angular positions;
   d) smoothing the N mean values of attenuations from one channel to the next with respect to each of the P principal angular positions, thereby obtaining a curve of response of attenuation as a function of the position of the channel, thereby eliminating high-frequency components, said response curve thus obtained representing the real variation of the attenuation introduced by the standard as a function of the respective position of the N channels;

wherein there are an even number of P principal angular positions and said positions form pairs that are 180 degrees apart and wherein the mean values of attenuations for the detection channels of each member of each said pair are determined by adding together attenuation values of both members of each said pair.

2. A method of calibration according to claim 1, wherein the smoothing step includes a filtering step.

3. A method of calibration according to claim 2, wherein the smoothing step further includes a polynomial approximating step performed on the curve which results from filtering.

4. A method of calibration according to claim 2 or claim 3, wherein the filtering step consists in forming the Fourier transform of the N mean values corresponding to one of the P principal angular positions, in filtering said Fourier transform to form a filtered Fourier transform, thereby eliminating the high-frequency components, and then forming the inverse Fourier transform of said filtered Fourier transform.

5. A method according to claim 1, wherein the standard has a shape which is symmetrical with respect to two axes and wherein mean values are determined for attenuations corresponding to symmetrical positions of the standard with respect to said axes.

6. A method according to claim 1, wherein said X-ray scanner includes:
   first means for computing the logarithm of the N signals delivered by the N detectors;
   second means for computing for each channel the attenuation introduced by the standard;
   third means for computing for each channel the mean value of the n measured attenuations with respect to a given principal angular position;
   fourth means for computing the Fourier transform of the N mean attenuations corresponding to a principal angular position;
   fifth means for eliminating the high-frequency components in the spectrum resulting from the Fourier transform;
   sixth means for computing the inverse Fourier transform of the low-frequency components of the spectrum;
   seventh means for computing a polynomial approximation of the curve resulting from the inverse Fourier transform;
   and means for retaining in memory the values representing the polynomial approximation of each response curve relative to a principal angular position.

7. A method of calibration according to claim 1, wherein mean values of attenuation for each of the N detectors are determined for a selected principal angular position, by adding together all attenuation values associated with principal angular positions having, for each channel in said N-channel detection device, an equivalent path length that x-rays must travel through the standard, in order to be detected by said channel.

* * * * *